United States Patent [19]

Gubin et al.

[11] Patent Number: 5,028,710
[45] Date of Patent: Jul. 2, 1991

[54] PROCESS FOR THE PREPARATION OF DERIVATIVES OF SULFONYL INDOLIZINE AND THEIR USE AS SYNTHETIC INTERMEDIATES

[75] Inventors: Jean Gubin, Brussels; Jean Lucchetti, Chastre, both of Belgium

[73] Assignee: Sanofi, Paris, France

[21] Appl. No.: 534,499

[22] Filed: Jun. 8, 1990

Related U.S. Application Data

[63] Continuation-in-part of Ser. No. 374,785, Jul. 3, 1989, abandoned.

[30] Foreign Application Priority Data

Jul. 4, 1988 [FR] France .............................. 88 09023

[51] Int. Cl.$^5$ .......................................... C07D 471/04
[52] U.S. Cl. .................................. 546/183; 544/127; 544/362
[58] Field of Search ................. 546/183; 544/127, 362

[56] References Cited

FOREIGN PATENT DOCUMENTS 0235111  9/1987  European Pat. Off. .

Primary Examiner—Bernard I. Dentz

Attorney, Agent, or Firm—Wegner, Cantor, Mueller & Player

[57] ABSTRACT

The object of the invention is a process for the preparation of derivatives of 3-sulfonyl indolizine of general formula:

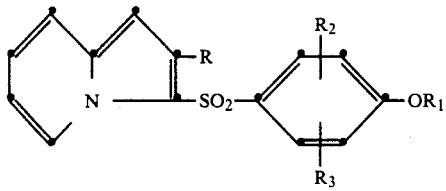

in which:
R is selected from hydrogen, alkyl, cycloalkyl, substituted or unsubstituted phenyl,
$R_1$ is a protecting group for hydroxyl,
$R_2$ and $R_3$, identical or different, is each selected from hydrogen, methyl or ethyl or halogen.

These compounds are intermediates which can be used for the preparation of 3-aminoalkoxyphenylsulfonyl-indolizines, which are useful in the treatment of certain diseases of the cardiovascular system.

8 Claims, No Drawings

PROCESS FOR THE PREPARATION OF DERIVATIVES OF SULFONYL INDOLIZINE AND THEIR USE AS SYNTHETIC INTERMEDIATES

This is a continuation-in-part of Ser. No. 374,785, filed 7/03/89, which is now abandoned.

Generally speaking, the present invention relates to the preparation of 3-aminolkoxyphenylsulfonyl-indolizine derivatives and, more especially, to novel synthetic intermediates and a process for their preparation.

More precisely, the invention relates to derivatives of 3-sulfonyl-indolizine of general formula:

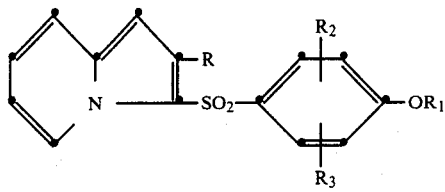

in which: R is selected from hydrogen, $C_1$-$C_8$ alkyl, linear or branched, $C_3$-$C_6$ cycloalkyl or unsubstituted phenyl or phenyl substituted by one or more substituents, identical or different, selected from halogen, for example fluorine, chlorine, bromine, and $C_1$-$C_4$ alkyl, $C_1$-$C_4$ alkoxy or nitro.

$R_1$ is a protecting group for hydroxyl, namely methyl, benzyl, $C_1$-$C_4$ alkylsulfonyl, for example methanesulfonyl, or $C_6$-$C_{10}$ arylsulfonyl, for example benzenesulfonyl or p-toluenesulfonyl.

$R_2$ and $R_3$, identical or different, is each selected from hydrogen, methyl or ethyl or halogen.

By "$C_1$-$C_8$ alkyl, linear or branched" is meant in particular methyl, ethyl, n-propyl, isopropyl, n-butyl, isobutyl, tert. butyl, n-pentyl, neopentyl, n-hexyl, n-heptyl or n-octyl.

Similarly, by "$C_3$-$C_6$ cycloalkyl" is meant in particular cyclopropyl or cyclohexyl.

Thus, in the light of the meanings given above R may be in particular methyl, ethyl, n-propyl, isopropyl, n-butyl, isobutyl, tert. butyl, 1-methylpropyl, n-pentyl, neopentyl, phenyl, monofluoro-, monochloro- or monobromo-phenyl, difluoro-, dichloro- or dibromo-phenyl, monomethyl- or dimethyl-phenyl, monomethoxy- or dimethoxy-phenyl or methylphenyl substituted by halogen.

Of the compounds of formula I, those in which R is isopropyl or cyclopropyl constitute preferred compounds.

Contrary to what might have been expected the preparation of the compounds of formula I has been successfully accomplished in a particularly straight forward manner.

Thus, another object of the present invention is an unexpected process for the preparation of the compounds of formula I.

The indolizine derivatives of formula I are particularly useful as intermediates, particularly for the preparation of 3-aminoalkoxyphenylsulfonyl-indolizine derivatives of general formula:

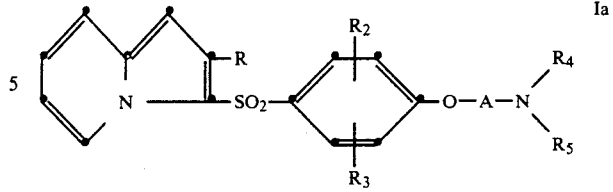

as well as their pharmaceutically acceptable salts, in which R, $R_2$ and $R_3$ are as defined previously, A is $C_2$-$C_5$ alkylene, linear or branched or 2-hydroxypropylene in which the hydroxy is optionally substituted by $C_1$-$C_4$ alkyl, $R_4$ is $C_1$-$C_8$ alkyl, linear or branched, or a radical of formula:

$$-Alk-R_6$$

in which Alk is a simple bond or $C_1$-$C_5$ alkylene, linear or branched, and $R_6$ is selected from pyridyl, phenyl, 2,3-methylenedioxyphenyl, 3,4-methylenedioxyphenyl or phenyl substituted by one or more substituents, identical or different, selected from halogen, $C_1$-$C_4$ alkyl or $C_1$-$C_4$ alkoxy, $R_5$ is selected from hydrogen or $C_1$-$C_8$ alkyl or $R_4$ and $R_5$, when they are taken together, are a $C_3$-$C_6$ alkylene or alkenylene optionally substituted by phenyl or optionally separated by —O—, —N= or —N—$R_7$, $R_7$ being selected from hydrogen, $C_1$-$C_4$ alkyl or phenyl.

These compounds of formula Ia have been shown to be endowed with remarkable pharmacological properties, in particular, inhibitory properties of calcium translocation as well as bradycardia-inducing, hypotensive and antiadrenergic properties. These properties, taken together, make the compounds in question particularly useful in the treatment of certain pathological syndromes of the cardiovascular system, in particular in the treatment of angina pectoris, hypertension, arrhythmia and cerebral circulatory insufficiency.

From this point of view, one of the most representative compounds of formula Ia is 2-isopropyl 3-[4-{3-[N-methyl-N-(3,4-dimethoxy-β-phenethyl)amino]-propyloxy}phenylsulfonyl] indolizine and its pharmaceutically acceptable salts.

The oxidation of indolizinyl sulfides to the corresponding sulfones has been little studied up to the present, probably on account of the well-known degradation of the indolizine ring by oxidizing agents. The opening of the indolizine ring to give picolinic acid —N-oxide and higher homologues as a result of the action of hydrogen peroxide in acetic acid has, for example, been described in "Heterocyclic Systems with Bridgehead Nitrogen Atoms", Part one, Intersc. Publ., New York, 1961 p. 263.

However, mention was made in the European patent application No. 235.111 of the oxidation of derivatives of 1-(4-aminoalkoxyphenylthio) indolizine to the corresponding sulfoxide derivatives by means of sodium periodate, potassium permanganate or 3-chloroperbenzoic acid, the reaction being conducted in water or methylene chloride. It has also been pointed out that during this oxidation, the corresponding sulfonyl derivative may possibly be formed without, however, any example being given to illustrate this assertion.

Within the framework of the development of the present invention, the behaviour of a 2-alkyl 3-p-methoxyphenyl indolizine, in this case the 2-isopropyl derivative, has been studied on reaction with different oxidizing agents.

The results obtained have shown that the use of the sodium periodate/potassium permanganate couple in an acetone/water mixture does not lead to the formation of the sulfone in question.

In order to diminish the oxidative power, potassium permanganate has also been used in the presence of a phase transfer catalyst. Preliminary experiments carried out in dichloromethane with or without the addition of acetic acid ended in failure.

Negative results were also recorded when sodium perborate was used in acid or basic solution or hydrogen peroxide was used in basic medium. Finally, the use of oxone (a mixture of the sulfate, hydrogen sulfate and hydrogen persulfate of potassium) in methanol/water medium has made it possible to detect the desired sulfone only in trace amounts.

In a surprising manner, it has now been found that it is possible to carry out the oxidation of 3-phenylthio indolizines by means of 3-chloroperbenzoic acid in high yields by bringing about the preferred formation of the corresponding sulfone to the detriment of the corresponding sulfoxide derivative or other by-products.

Thus, the process of the invention for the preparation of the indolizine derivatives of formula I consists of oxidizing, at room temperature, a 3-phenylthio indolizine of general formula:

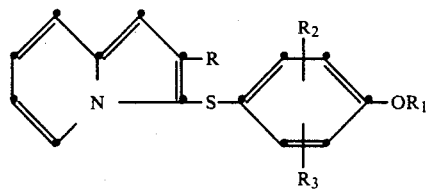

in which R, $R_1$, $R_2$ and $R_3$ are as defined previously, by means of 3-chloroperbenzoic acid in the presence of a basic reagent, usually an alkali metal carbonate such as sodium or potassium carbonate, in a $C_1$–$C_4$ alcohol as solvent, and preferably methanol.

Usually, 1 to 5 equivalents, and preferably 4 equivalents, of 3-chloroperbenzoic acid are used per equivalent of 3-phenylthio indolizine derivative of formula II and 2 to 4 equivalents, and preferably about 2.5 equivalents of basic reagent are used per equivalent of 3-chloroperbenzoic acid.

In the particular case of the preparation of 2-isopropyl 3-p-methoxyphenylsulfonyl indolizine, the preocess of the invention makes it possible to obtain yields of the order of 50 to 55%.

The compounds of formula II can be obtained by reacting at reflux and in an appropriate solvent such as an alcohol, for example ethanol, an indolizine possessing a substituent R at position 2 (hereafter called 2-R indolizine) with a disulfide of general formula:

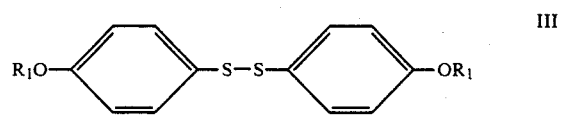

in which $R_1$ is as defined previously.

The compounds of formula III are known compounds which have been published in Bull. Soc. Chim. Fr. 33 p. 837 or which can be prepared by the method described there.

Similarly, the 2-R indolizines are known compounds which have been published in the French Pat. No. 2.341.578.

As pointed out previously, a series of preliminary experiments were carried out with the intention of preparing 2-isopropyl 3-p-methoxyphenylsulfonyl indolizine starting from 2-isopropyl 3-p-methoxyphenylthio indolizine by using different oxidizing reagents and different reaction media.

For this purpose, the following process was used:

A solution of one equivalent of 2-isopropyl 3-p-methoxyphenylthio indolizine is stirred at room temperature in the presence of an oxidizing reagent while varying:
 the reaction medium
 the amount of oxidizing reagent
and, if necessary, the medium is heated at reflux, then the compounds formed are separated by thin layer chromatography (solvent:ethyl acetate/hexane 3/7).

The following results were obtained in a comparative study with the process of the invention:

| Oxidizing agent | | | | | | | | |
|---|---|---|---|---|---|---|---|---|
| Nature | Number of equivalents | Reaction media | I* (%) | II* (%) | III* (%) | IV* (%) | V* (%) | VI* (%) |
| (1) Preliminary experiments | | | | | | | | |
| $NaBO_3$ | 10 | Methanol/water NaOH | 100 | — | — | — | — | — |
|  | 5 | Acetic acid | 2 | — | — | — | 19 | maj.* |
| $NaIO_4$/$KMnO_4$ 1/1 | 1 | Acetone/water | min.* | maj. | — | — | — | maj. |
| $KMnO_4$ (+ phase transfer catalyst)* | 3 | Dichloromethane | 100 | — | — | — | — | — |
|  | 3 | Dichloromethane/ acetic acid | — | min. | — | — | min. | maj. |
| $H_2O_2$ | 6 | Methanol/water | maj. | traces | — | — | — | — |
| Oxone | 3 | Methanol/water | maj. | — | traces | — | maj. | min. |
|  | 6 | Methanol/water | — | — | traces | — | maj. | min. |
|  | 2 | Methanol/water/ $H_2SO_4$ | 9 | — | 2 | — | 48 | — |
|  | 6 | Methanol/water/ | min. | 20 | 7 | — | — | — |

-continued

| Oxidizing agent | | | | | | | | |
|---|---|---|---|---|---|---|---|---|
| Nature | Number of equivalents | Reaction media | I* (%) | II* (%) | III* (%) | IV* (%) | V* (%) | VI* (%) |
| 3-chloro perbenzoic acid | 2 | K$_2$CO$_3$ Methanol | 2 | 10 | 1 | 7 | 32 | min. |
| (2) Process of the invention | | | | | | | | |
| 3-chloro perbenzoic acid | 4 | Methanol/ K$_2$CO$_3$ | 29 | 9 | 53 | — | — | — |

I: 2-isopropyl 3-p-methoxyphenylthio indolizine
II: 2-isopropyl 3-p-methoxyphenylsulfoxide indolizine
III: 2-isopropyl 3-p-methoxyphenylsulfonyl indolizine
IV: 2-isopropyl 1-p-methoxyphenylsulfoxide indolizine
V: bis-(p-methoxyphenyl)-thiosulfonate
VI: unidentified products
maj.: major product
min.: minor product
phase transfer catalyst: tris[2-(2-methoxyethoxy)ethyl]amine These results show that only the process of the invention makes it possible to obtain high yields of the 3-sulfonyl indolizine derivative of formula I.

On the other hand, these results clearly demonstrate the importance of a basic medium for the efficient implementation of the oxidation process of the invention.

As pointed out previously, the 3-sulfonyl indolizine derivatives of formula I can be used as synthetic intermediates for the preparation of indolizine derivatives of formula Ia above.

Thus the compounds of formula Ia can be obtained by implementing a process comprising:

a) the deprotection of the p-hydroxyphenylsulfonyl group
  when R$_1$ is methyl, by treatment by means of an ethanethiol/aluminium chloride mixture,
  when R$_1$ is benzyl, by treatment by means of hydrogen in the presence of a catalyst such as Raney nickel or palladium on charcoal,
  when R$_1$ is alkylsulfonyl or arylsulfonyl, by treatment in basic medium in order to obtain the p-hydroxyphenylsulfonyl derivatives of general formula:

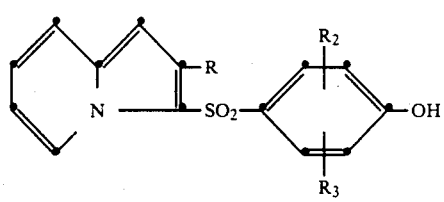

IV in which R$_1$, R$_2$ and R$_3$ are as defined previously, b) the condensation of the compound of formula IV with an alkane dihalide of general formula:

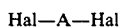

Hal—A—Hal V in which A is alkylene as defined in formula Ia and Hal is halogen, at reflux in a solvent such as methyl-ethyl-ketone or N,N-dimethylformamide in the presence of a basic reagent, or alternatively b$_1$) the condensation of the compound of formula IV with a halogenated alcohol of general formula:

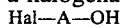

Hal—A—OH VI in which A is alkylene as defined in formula Ia and Hal is as defined previously, in a solvent such as N,N-dimethylformamide in the presence of a basic reagent, then condensation of the alcohol derivative obtained with a halide of general formula:

Hal—W VII in which W is selected from C$_1$-C$_4$ alkylsulfonyl, for example methanesulfonyl, or C$_6$-C$_{10}$ arylsulfonyl, for example benzenesulfonyl or p-toluenesulfonyl, in an acid-acceptor solvent such as pyridine or alternatively (b$_2$) the heating at reflux of the compound of formula IV with an epihalohydrin such as epichlorohydrin or epibromohydrin in the presence of a basic reagent and in a polar solvent such as methyl-ethyl-ketone in order to obtain the 3-sulfonyl indolizine derivatives of general formula:

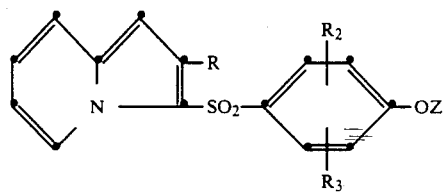

VIII in which R, R$_2$ and R$_3$ are as defined previously and Z is selected from oxiranylmethylene or a radical of formula:

—A—Z$_1$ in which A is C$_2$-C$_5$ alkylene, linear or branched, and Z$_1$ is selected from halogen, C$_1$-C$_4$ alkylsulfonyloxy or C$_6$-C$_{10}$ arylsulfonyloxy.

The basic reagent used for the treatment of the compound of formula IV is usually an alkali metal carbonate, for example potassium carbonate, an alkali metal hydroxide such as sodium or potassium hydroxide, an alkali metal hydride such as sodium hydride or an alkali metal alcoholate such as sodium methylate or ethylate.

The derivative of formula VIII is reacted with an amine of general formula:

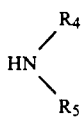

in which $R_4$ and $R_5$ are as defined previously, the reaction optionaly taking place in the presence of an acid acceptor and in a suitable solvent, usually a polar solvent such as an alcohol, for example butanol, a ketone such as methyl-ethyl-ketone, an aromatic hydrocarbon such as benzene, toluene or xylene, or dimethylsulphoxide or even an excess of the amine of formula VIII in order to obtain the compounds of formula Ia in the form of the free base which is reacted, if desired, with a suitable acid in order to form a pharmaceutically acceptable salt of this compound.

According to an alternative method, the compounds of formula IV may be used by treating such a compound directly with a halide of general formula:

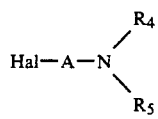

in which Hal, $R_4$ and $R_5$ are as defined previously and A is $C_2$-$C_5$ alkylene such as defined previously, the reaction being conducted in the presence of a basic reagent such as an alkali metal carbonate, for example potassium carbonate, an alkali metal hydroxide such as sodium or potassium hydroxide, an alkali metal hydride such as sodium hydride or an alkali metal alcoholate such as sodium methylate or ethylate in order to obtain the compounds of formula I in which A is $C_2$-$C_5$ alkylene.

The following non-limiting examples illustrate the process of the invention as well as the use of the indolizine derivatives of formula I for the preparation of the compounds of formula Ia:

EXAMPLE 1

Preparation of 2-isopropyl 3-p-methoxyphenylsulfonyl indolizine.

a) 2-isopropyl 3-p-methoxyphenylthio indolizine

A mixture of 25.2 g (0.158 mole) of 2-isopropyl indolizine and 44 g (0.158 mole) of bis-(4-methoxyphenyl) disulfide is heated at reflux in 500 ml of ethanol for 90 h. When the reaction is over, the mixture is allowed to cool and evaporate to dryness. The residue is taken up in either and the solution is extracted with a 5% solution of sodium hydroxide. It is washed with water, dried and decolorized with active charcoal. It is filtered and evaporated to dryness and the residue obtained is purified by elution chromatography on silica using carbon tetrachloride as eluant.

In this manner, 14 g of 2-isopropyl 3-p-methoxyphenylthio indolizine are obtained in the form of crystals after recrystallization from hexane.

Yield: 27%

Purity: 98.3% (high performance liquid chromatography).

M.p.: 59°–60° C.

(b) 2-isopropyl 3-p-methoxyphenyl sulfonyl indolizine 1 g ($3.36.10^{-3}$ mole) of 2-isopropyl 3-p-methoxyphenylthio indolizine is dissolved in 60 ml of methanol, then 3.36 g ($33.6.10^{-3}$ mole) of potassium carbonate are added followed by 2.4 g ($12.34.10^{-3}$ mole) of 88.7% 3-chloroperbenzoic acid. The mixture is stirred for 4 hours at room temperature, poured into 100 ml of water and then the mixture is extracted several times with ethyl acetate. The organic phase is dried over anhydrous magnesium sulfate, filtered and concentrated in a vacuum. The oil obtained is eluted from a column of silica by using an ethyl acetate/hexane 30/70 mixture as eluant.

In this manner, 2-isopropyl 3-p-methoxyphenylsulfonyl indolizine is obtained in a yield of 53%.

M.p.: 103.5° C. (isopropanol)

| | Elemental analysis | | | |
|---|---|---|---|---|
| | C% | H% | N% | S% |
| Calculated | 65.63 | 5.81 | 4.25 | 9.73 |
| Found | 65.44 | 5.76 | 4.33 | 9.86 |

I.R. Spectrum (KBr): 1320 cm$^{-1}$: asymmetrical stretching of $SO_2$ 1145 cm$^{-1}$: symmetrical stretching of $SO_2$ N.M.R. Spectrum: δ: 1.1–1.5 ppm (6H). 3.6–4.2 ppm (4H) 6.3–6.5 ppm (1H) 6.5–7.1 ppm (4H) 7.2–7.5 ppm (1H) 7.6–7.9 ppm (2H) 8.7–8.9 ppm (1H)

The following example illustrates the preparation of a 3-aminoalkoxphenylsulfonyl indolizine derivative of formula Ia:

EXAMPLE I

Preparation of 2-isopropyl 3-[4-{3-[N-methyl-N-(3,4-dimethoxy-β-phenethyl-)amino] propyloxy}phenylsulfonyl] indolizine oxalate a) 2-isopropyl 3-p-hydroxyphenylsulfonyl indolizine 6.7 g (0.050 mole) of aluminium chloride are suspended in 100 ml of dichloromethane and 25 ml of ethanethiol. This suspension is stirred and cooled to 0° C. while 2.5 g of 2-isopropyl 3-p-methoxyphenylsulfonyl indolizine in dichloromethane are added. The addition takes about 15 minutes. The reaction mixture is allowed to warm to room temperature and maintained there for 45 minutes. It is poured onto ice, then 5 ml of concentrated hydrochloric acid are added with stirring. The mixture is extracted with 2 fractions of ethyl ether and the ethereal extracts are pooled. They are washed with 3 fractions of 30 ml of a 10% aqueous solution of sodium bicarbonate and the aqueous phase is acidified.

In this manner, crude 2-isopropyl 3-p-hydroxphenylsulfonyl indolizine is obtained.

b) 2-isopropyl 3-[4-{3[N-methyl-N-(3,4-dimethoxy-β-phenethyl)amino]propyloxy}phenylsulfonyl] Indolizine oxalate.

0.510 g ($1.57.10^{-3}$ mole) of 2-isopropyl 3-p-hydroxyphenylsulfonyl indolizine, 0.5 g of potassium carbonate and 5 ml of dimethylsulfoxide are stirred at room temperature for 30 minutes. 0.524 g ($1.45.10^{-3}$ mole) of 1-chloro 3-[N-methyl-N-(3,4-dimethoxy-β-phenethyl) amino]propane oxalate, an added to this mixture,. Stirring is maintained for 26 h at room temperature then for 2 h at 50° C. The dimethylsulfoxide is romoved in a vacuum and the residue is taken up in water. The mixture is extracted twice with ethyl acetate, the extracts are washed twice with water and dried over sodium sulfate. After filtration, the filtrate is evaporated in a vacuum to give 0.845 g of an amber-colored oil. This oil is purified on a column of silica using, as eluants, ethyl acetate containing 5%, 10% and then 20% of methanol, which leads to 0.583 g of the desired product in the form of the free base.

(yield: 73%; purity: 99.4%).

The oxalate is then formed by using 0.530 g of the base thus obtained and a solution of oxalic acid in ethyl ether. The oxalate formed is then recrystallized from a mixture of ethyl acetate/methanol/ethyl ether.

In this manner, 0.473 g of 2-isopropyl 3-[4-{3-[N-methyl-N-(3,4-dimethoxy-β-phenethyl)amino]-propyloxy}phenylsulfonyl]indolizine oxalate is obtained in the form of a white solid. M.p.: 135°–137° C.

EXAMPLE II

Preparation of 2-isopropyl-3-[4-{3-(tert-butylamino) Propyloxy}Benzenesulphonyl]Indolizine hydrochloride a) 2-isopropyl-3-[4-(3-bromopropyloxy)benzenesulphonyl]indolizine While stirring 1.6 g ($5.07 \times 10^{-3}$ mol) of 2-isopropyl-3-(4-hydroxybenzenesulphonyl)indolizine prepared according to Example Ia), 0.8 g ($5.6 \times 10^{-3}$ mol) of potassium carbonate and 4.1 g ($20.2 \times 10^{-3}$ mol) of 1,3-dibromopropane are slightly refluxed in 30 ml of methyl-ethyl-ketone. After 24 hours, the medium was cooled and filtered to eliminate the mineral salts and the filtrate was isolated under vacuum and then under high vacuum to eliminate the 1,3-dibromopropane in excess.

The oily residue was taken up in water containing sodium hydroxide and the brominated product was extracted to provide 1 g of a compound which was purified on a silica column using dichloromethane as eluent.

In this manner, 0.9 g of 2-isopropyl-3-[4-(3-bromopropyloxy)benzenesulphonyl]indolizine was obtained in the form of a greenish oil which solidified after some days.

Yield: 40.67%.

b) 2-isopropyl-3-{4-[3-(tert-butylamino)propyloxy] Benezenesulphonyl}Indolizine hydrochloride A mixture of 0.9 g ($2.06 \times 10^{-3}$ mol) of 2-isopropyl-3-[4-(3-bromopropyloxy)benzenesulphonyl] Indolizine and 0.76 g ($10.3 \times 10^{-3}$ mol) of tert-butylamine in 4 ml of dimethylsulphoxide are stirred for 48 hours at room-temperature. The dimethylsulphoxide was eliminated under vacuum together with the tert-butylamine in excess and the residue was taken up in water containing sodium hydroxide.

The medium was then extracted with dichloromethane to give 0.8 g of a yellow oil which was purified on an alumina column using an ethyl acetate/methanol 95/5 mixture as eluent. The oil so obtained (0.65 g) was then transformed into the hydrochloride which was recrystallized from ethyl acetate/methanol.

In this manner, 0.520 g of 2-isopropyl-3-{4-[3-(tert-butylamino)propyloxy]benzenesulphonyl}indolizine hydrochloride was obtained in the form of a white solid.

Yield: 54,3%

MP: 198°–200° C.

We claim:

1. Process for the preparation of 3-sulfonyl indolizine compounds of general formula:

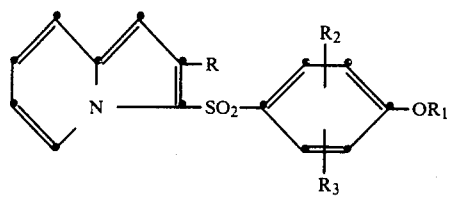

in which:
R is selected from hydrogen, $C_1$–$C_8$ alkyl, linear or branched, $C_3$–$C_6$ cycloalkyl or unsubstituted phenyl or phenyl substituted by one or more substituents, identical or different, selected from halogen, $C_1$–$C_4$ alkyl, $C_1$–$C_4$ alkoxy or nitro, $R_1$ is a protecting group for hydroxyl, namely methyl, benzyl, $C_1$–$C_4$ alkylsulfonyl or $C_6$–$C_{10}$ arylsulfonyl, $R_2$ and $R_3$, identical or different, is each selected from hydrogen, methyl or halogen, wherein a 3-phenylthio indolizine compound of general formula:

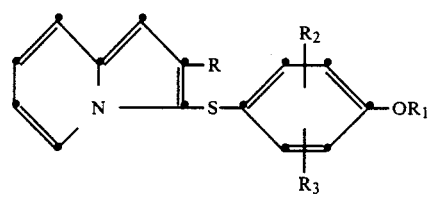

in which R, $R_1$, $R_2$ and $R_3$ are as defined previously, is oxidized at room temperature by means of 3-chloroperbenzoic acid in the presence of a basic reagent and in a $C_1$–$C_4$ alcohol as solvent.

2. Process according to claim 1, wherein the basic reagent is an alkali metal carbonate.

3. Process according to claim 1, wherein the solvent is methanol.

4. Process according to claim 1, wherein 1 to 5 equivalents of 3-chloroperbenzoic acid are used per equivalent of 3-phenylthio indolizine derivative of formula II.

5. Process according to claim 4, wherein 4 equivalents of 3-chloroperbenzoic acid are used.

6. Process according to claim 1, wherein 2 to 4 equivalents of basic reagent are used per equivalent of 3-chloroperbenzoic acid.

7. Process for the preparation of a 3-aminoalkoxyphenyl-sulfonyl indolizine compound of general formula:

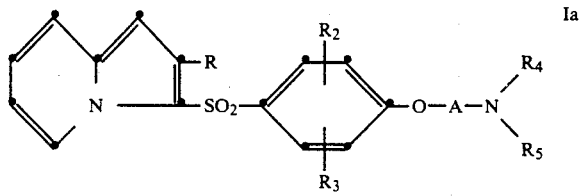

as well as its pharmaceutically acceptable salts, in which

R is selected from hydrogen, $C_1$–$C_8$ alkyl, linear or branched, $C_3$–$C_6$ cycloalkyl or unsubstituted phenyl or phenyl substituted by one or more substituents, identical or different, selected from halogen, $C_1$–$C_4$ alkyl, $C_1$–$C_4$ alkoxy or nitro, $R_2$ and $R_3$, identical or different, is each selected from hydrogen, methyl or halogen, A is selected from $C_2$-$C_5$ alkylene, linear or branched, or 2-hydroxy propylene in which the hydroxy is optionally substituted by a $C_1$-$C_4$ alkyl, $R_4$ is selected from $C_1$-$C_8$ alkyl, linear or branched, or a radical of formula:

—ALK—$R_6$ in which ALK is selected from a simple bond or $C_1$-$C_5$ alkylene, linear or branched, and $R_6$ is selected from pyridyl, phenyl, 2,3-methylene-dioxyphenyl, 3,4-methylenedioxyphenyl, or phenyl substituted by one or more substituents, identical or different, selected from halogen, $C_1$-$C_4$ alkyl or $C_1$-$C_4$ alkoxy, $R_5$ is selected from hydrogen or $C_1$-$C_8$ alkyl or $R_4$ and $R_5$, when they are taken together, are $C_3$-$C_6$ alkylene or alkenylene, optionally substituted by phenyl or optionally separated by —O—, —N= or —N—$R_7$, $R_7$ being selected from hydrogen, $C_1$-$C_4$ alkyl or phenyl, wherein a) a 3-phenylthio indolizine compound of general formula

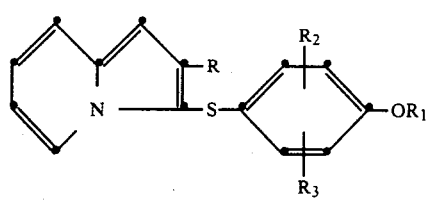

II in which R, $R_2$ and $R_3$ are as defined previously and $R_1$ is a protecting group for hydroxyl, namely methyl, benzyl, $C_1$-$C_4$ alkylsulfonyl or $C_6$-$C_{10}$ arylsulfonyl, is oxidized at room temperature by means of 3-chloroperbenzoic acid in the presence of a basic reagent and in a $C_1$-$C_4$ alcohol as solvent to provide a 2-sulfonyl indolizine compound of general formula:

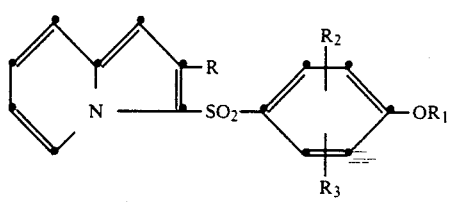

I in which R, $R_1$, $R_2$ and $R_3$ are as defined previously;

b) deprotection of the p-hydroxyphenylsulfonyl group of the compound of formula I as defined previously is carried out in order to obtain a p-hydroxyphenylsulfonyl derivative of general formula:

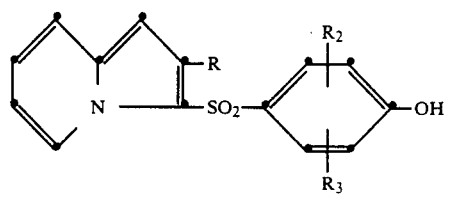

IV in which R, $R_2$ and $R_3$ are as defined previously;

c) the condensation of the compound of formula IV is carried out with an alkane dihalide of general formula:

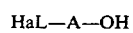   V in which A is alkylene as defined in formula Ia and Hal is halogen, at reflux in a solvent in the presence of a basic reagent, or alternatively $c_1$) the condensation of the compound of formula IV with a halogenated alcohol of general formula:

   VI in which A is alkylene as defined in formula Ia and HaL is a defined previously, is carried out in a solvent in the presence of a basic reagent, followed by the condensation of the alcohol derivative obtained with a halide of general formula:

HaL—W   VII in which W is selected from $C_1$-$C_4$ alkylsulfonyl or $C_6$-$C_{10}$ arylsulfonyl, in an acid-acceptor solvent, or alternatively $c_2$) the heating at reflux of the compound of formula IV with an epihalohydrin such as epichlorhydrin or epibromohydrin is carried out in the presence of a basic reagent in a polar solvent in order to obtain a 3-sulfonyl indolizine derivative of general formula:

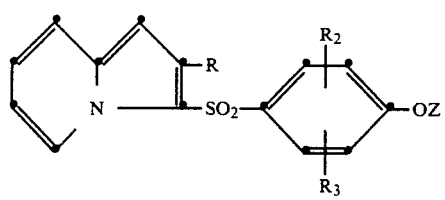

VIII in which R, $R_2$ and $R_3$ are as defined previously and Z is selected from oxiranylmethyl or a radical of formula:

—A—$Z_1$ in which A is $C_2$-$C_5$ alkylene, linear or branched, and $Z_1$ is selected from halogen, $C_1$-$C_4$ alkylsulfonyloxy or $C_6$-$C_{10}$ arylsulfonyloxy;

d) the derivative of formula VIII is reacted with an amine of general formula:

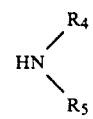   IX in which $R_4$ and $R_5$ are as defined previously, the reaction taking place in the presence of an acidacceptor in a suitable solvent in order to obtain a compound of formula Ia in the form of the free base which may be reacted, if desired, with a suitable acid in order to form a pharmaceutically acceptable salt of this compound.

8. - Process for the preparation of a 3-aminoalkoxyphenyl-sulfonyl indolizine derivative of general formula:

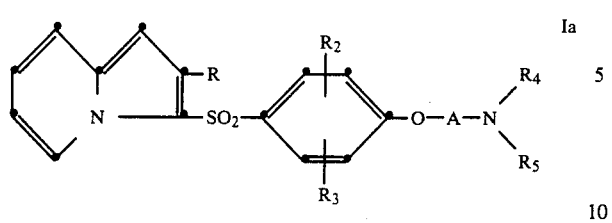

as well as its pharmaceutically acceptable salts in which

R is selected from hydrogen, $C_1$–$C_8$ alkyl, linear or branched, $C_3$–$C_6$ cycloalkyl or unsubstituted phenyl or phenyl substituted by one or more substituents, identical or different, selected from halogen, $C_1$–$C_4$ alkyl, $C_1$–$C_4$ alkoxy or nitro, $R_2$ and $R_3$, identical or different, is each selected from hydrogen, methyl or halogen, A is $C_2$–$C_5$ alkylene, linear or branched, $R_4$ is selected from $C_1$–$C_8$ alkyl, linear or branched, or a radical of formula:

—Alk—$R_6$ in which

Alk is selected from a simple bond or $C_1$–$C_5$ alkylene, linear or branched, and $R_6$ is selected from pyridyl, phenyl, 2,3-methylenedioxy-phenyl, 3,4-methylenedioxyphenyl or phenyl substituted by one or more substituents, identical or different, selected from halogen, $C_1$–$C_4$ alkyl or $C_1$–$C_4$ alkoxy, $R_5$ is selected from hydrogen or $C_1$–$C_8$ alkyl or $R_4$ and $R_5$, when they are taken together, are $C_3$–$C_6$ alkylene optionally substituted by phenyl or optionally separated by —O—, —N= or —N—$R_7$, $R_7$ being selected from hydrogen, $C_1$–$C_4$ alkyl or phenyl, wherein a) a 3-phenylthio indolizine compound of general formula

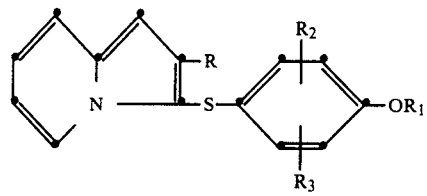

in which R, $R_2$ and $R_3$ are as defined previously and $R_1$ is a protecting group for hydroxyl, namely methyl, benzyl, $C_1$–$C_4$ alkylsulfonyl or $C_6$–$C_{10}$ arylsulfonyl, is oxidized at room temperature by means of 3-chloroperbenzoic acid in the presence of a basic reagent and in a $C_1$–$C_4$ alcohol as solvent to provide a 2-sulfonyl indolizine compound of general formula:

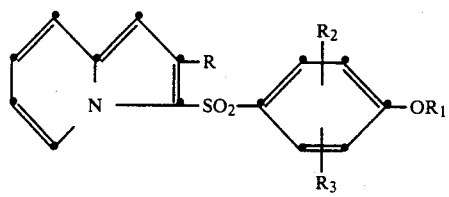

in which R, $R_1$, $R_2$ and $R_3$ are as defined previously;

b) deprotection of the p-hydroxyphenylsulfonyl group of a compound of formula I as defined previously is carried out in order to obtain a p-hydroxyphenylsulfonyl derivative of general formula:

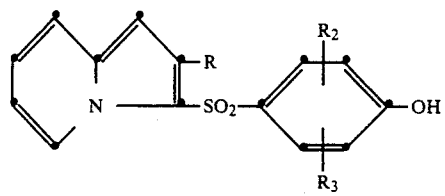

in which $R_1$, $R_2$ and $R_3$ are as defined previously and; c) the compound of formula IV is treated with a halide of general formula:

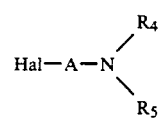

in which HaL, $R_4$ and $R_5$ are as defined previously and A is $C_2$–$C_5$ alkylene, the reaction being conducted in the presence of a basic reagent.

* * * * *